United States Patent [19]

Megison et al.

[11] Patent Number: 4,781,710

[45] Date of Patent: Nov. 1, 1988

[54] ABSORBENT PAD HAVING IMPROVED LIQUID DISTRIBUTION

[75] Inventors: Donald R. Megison; Richard A. Vonderhaar, both of Cincinnati, Ohio

[73] Assignee: The Procter & Gamble Company, Cincinnati, Ohio

[21] Appl. No.: 50,815

[22] Filed: May 15, 1987

[51] Int. Cl.⁴ .............................................. A61K 13/16
[52] U.S. Cl. ..................... 604/378; 604/385.1
[58] Field of Search .............. 604/378, 380, 385, 374, 604/375

[56] References Cited

U.S. PATENT DOCUMENTS

| | | | |
|---|---|---|---|
| 2,788,003 | 4/1957 | Morin | 128/284 |
| 3,053,252 | 9/1962 | Wolf | 128/156 |
| 3,430,629 | 3/1969 | Murphy | 128/284 |
| 3,707,430 | 12/1972 | Costanza et al. | 161/123 |
| 3,721,242 | 3/1973 | Krusko | 128/287 |
| 3,903,890 | 9/1975 | Mesek et al. | 128/287 |
| 3,908,659 | 9/1975 | Wehrmeyer et al. | 128/287 |
| 3,971,381 | 7/1976 | Gibson | 128/296 |
| 4,145,464 | 3/1979 | McConnell et al. | 428/171 |
| 4,191,609 | 3/1980 | Trokhan | 162/113 |
| 4,259,387 | 3/1981 | Mesek | 428/167 |
| 4,443,512 | 4/1984 | Delvaux | 428/162 |
| 4,501,586 | 2/1985 | Holtman | 604/380 |
| 4,650,481 | 3/1987 | O'Connor et al. | 604/380 |

FOREIGN PATENT DOCUMENTS

0205242 12/1986 European Pat. Off. .

*Primary Examiner*—Stephen C. Pellegrino
*Attorney, Agent, or Firm*—John M. Pollaro; Frederick H. Braun; Richard C. Witte

[57] ABSTRACT

An absorbent pad having a densification pattern comprising relatively low density tuft regions which are separated and surrounded by channels. The channels further comprise storage regions and transport regions wherein one of said storage regions or said transport regions separate and surround the other of said storage regions or said transport regions. The transport regions have a density greater than the density of the storage regions which, in turn, have a density greater than the tuft regions.

9 Claims, 6 Drawing Sheets

ABSORBENT PAD HAVING IMPROVED LIQUID DISTRIBUTION

FIELD OF THE INVENTION

The present invention relates generally to densification patterns for absorbent pad structures.

BACKGROUND OF THE INVENTION

Absorbents pads fabricated of air-laid fiberized pulp lap and disposable diapers, incontinent briefs, underpads, and catamenial pads utilizing such pads are known in the prior art. Such air-laid structures may be formed on a paper tissue and an example of fiberizing or disintegrating pulp lap and felting thereof for manufacture of such a product is disclosed, for example, in U.S. Pat. No. 3,519,211 entitled "Disintegration Process For Fibrous Sheet Material", which patent issued to Sakulich, et al. on July 7, 1970, U.S. Pat. No. 3,750,962 entitled "Disintegration Process For Fibrous Sheet Material", which patent issued to Morgan, Jr. on Aug. 7, 1973, and U.S. Pat. No. 3,825,652 entitled "Apparatus For Preparing Airfelt", which patent issued to Buell on July 23, 1974. The disclosure of the aforesaid patents are hereby incorporated herein, by reference, as fully and completely as if physically reproduced hereat and throughout this application the terms "air-laid" and "airfelt" pads are intended to refer to a product such as that formed in accordance with said patents.

It has also been previously suggested to fully enclose such an air-laid felt pad or bat within a tissue envelope to aid in supporting the felt during processing, including converting, and to aid in preventing disintegration thereof during use. See, e.g., Kalwaites U.S. Pat. No. 3,444,859; Schutte U.S. Pat. No. 3,741,212; Costanza et al. U.S. Pat. No. 3,769,978.

It has also been recognized that increased wicking and fluid transfer or transport within such a structure may be accomplished by densifying or compressing the structure to provide an increased density thereof as suggested in, e.g., Duncan U.S. Pat. No. 3,592,194; Krusko U.S. Pat. No. 3,721,242; and DeKnight U.S. Pat. No. 3,769,978. It has even been suggested that a one-directional generally sinuous pattern of compressed narrow strips may produce enhanced distribution of moisture in such a structure longitudinally along such strips. However, such narrow compressed strips have also been recognized as barriers reducing transverse moisture transport and also resulting in a stiffer and less soft product. See, e.g., Morin U.S. Pat. No. 2,788,003. It has also been suggested that the compressed narrow strips may be arranged in various patterns, one such pattern comprising a plurality of intersecting lines. See, e.g., Mesek U.S. Pat. 4,259,387. Further, it has been suggested that compressing a pad of the general type referred to above so as to decrease the thickness thereof and increase the bulk density, not only creates increased wicking but, in addition, may produce increased flexibility. See, e.g., Gobbo, Sr. et al. U.S. Pat. No. 3,065,751. However, the mere increase in flexibility does not necessarily result in increased softness and what the prior art has apparently not recognized, is that softness and flexibility are not the same and, in fact, structures exhibiting high flexibility may provide a very low softness impression to a user. Moreover, the prior art has also apparently not recognized that subjective surface dryness impressions are not necessarily consistent with objective tests for surface dryness and, in fact, subjective surface dryness impressions may be diametrically opposite of objective surface dryness test results.

One invention that has made good progress in addressing the aforementioned concerns is disclosed in U.S. Pat. No. 3,908,659, entitled "Absorbent Pad Structure, Diaper Construction Utilizing Same and Methods of Manufacture Thereof", which patent issued to Wehrmeyer et al. on Sept. 30, 1975. U.S. Pat. No. 3,908,659 discloses an embossing pattern for an absorbent core, which pattern is formed by dry pattern densification, and which pattern comprises an array of generally circular low density tufts which are separated and surrounded by bilaterally extending non-linear and generally sinuous regions of higher density. Such a pattern provides high softness impression together with high moisture wicking and transport and high surface dryness impression.

Bearing in mind the foregoing, it is a primary object of the present invention to provide a novel and improved absorbent pad structure.

Another primary object of the present invention, in addition to the foregoing object, is to provide such novel and improved absorbent pad structures having optimized liquid distribution and wicking capabilities as well as surface dryness and softness impressions.

Yet another primary object of the present invention, in addition to each of the foregoing objects, is the provision of such novel and improved absorbent pad structures particularly constituted for use in disposable diaper structures, underpad structures, incontinent brief structures, and catamenial pad structures fabricated thereof.

Yet still another primary object of the present invention, in addition to each of the foregoing object, is the provision of a novel absorbent pad having relatively low density tuft regions which are separated and surrounded by channels, wherein the channels comprise relatively intermediate density storage regions and relatively high density transport regions.

Yet still another primary object of the present invention, in addition to each of the foregoing objects, is the provision of a novel absorbent pad fabricated of airfelt, preferably within a tissue envelope, subjected to dry pattern densification, as by patterned compression, to provide a pattern of alternating horizontal rows in the longitudinal direction of rhombus shaped tuft regions and pairs of triangle tuft regions, wherein the rhombus and pairs of triangle shaped tuft regions are staggered in the lateral direction and are surrounded by bilaterally extending, linear and preferably sinuous channels. The channels comprise relatively high density transport regions which are separated and surrounded by relatively intermediate density storage regions which have a density greater than the density of the tuft regions but less than the density of the transport regions.

The invention resides in the combination, construction, arrangement and disposition of the various component parts and elements incorporated in improved absorbent pads constructed in accordance with the principles of this invention. The present invention will be better understood and objects and important features other than those specifically enumerated above will become apparent when consideration is given to the following details and description, which when taken in conjunction with the annexed drawings describes, discloses, illustrates and shows the preferred embodiment or modification of the present invention and what is presently considered and believed to be the best mode of practicing the principles thereof. Further embodiments and modifications may be suggested to those having the benefit of the teachings herein and such other embodiments or reserved especially as they fall within the scope and spirit of the subjoined claims.

SUMMARY OF THE INVENTION

In accordance with the present invention, an absorbent pad having improved liquid distribution and retention characteristics is provided. A pad made in accordance with the present invention has use in underpads, diapers, briefs, catamenial pads, and the like.

The absorbent pads of the present invention comprise a densification pattern wherein relatively low density tuft regions are separated and surrounded by channels. The channels further comprise storage regions and transport regions wherein one of said storage regions or said transport regions separate and surround the other of said storage regions or said transport regions. The transport regions have a density greater than the density of the storage regions which, in turn, have a density greater than the density of the tuft regions.

BRIEF DESCRIPTION OF THE DRAWINGS

While the specification concludes with claims particularly pointed out and distinctly claiming the subject matter which is regarded as forming the present invention, it is believed that the invention will be better understood from the following descriptions which are taken in conjunction with the accompanying drawings in which like designations are used to designate substantially identical elements and in which:

DETAILED DESCRIPTION OF THE PREFERRED EMBODIMENTS

The present invention relates to absorbent pad structures, and more particularly, to absorbent pad structures used in disposable diapers, incontinent briefs, underpads and catamenial pads, for absorbing and containing body exudates. The present invention is characterized by novel and improved densification patterns for absorbent pads.

Figure 1:
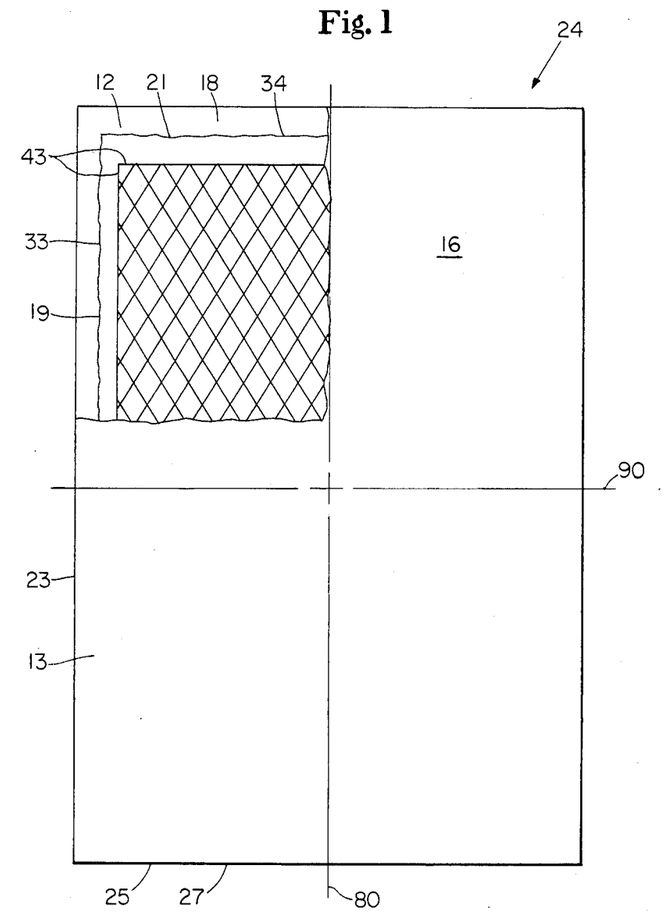
FIG. 1 is top plan view of an absorbent pad of the present invention which has been incorporated into an underpad having portions cut away to reveal underlining structure.

A preferred embodiment of an underpad structure 24 utilizing an absorbent pad 12 constructed in accordance with the principles of the present invention is shown in FIG. 1. It must be emphasized and understood that although the absorbent pad 12 will be described as it would be used in an underpad or bedpan, the present invention is not limited to such use. In particular, it is contemplated within the disclosure hereof that said pad could be used as an absorbent pad in a disposable diaper or an incontinent brief, such as a disposable diaper formed in accordance with the teachings of U.S. Pat. No. 3,860,003, entitled "Contractible Side Portions For Disposable Diaper," which patent issued to K. B. Buell on Jan. 14, 1975, and which patent is incorporated herein by reference as fully and completely as if physically reproduced hereat.

Further, while the present invention will be particularly described and shown herein as applied to an underpad, and as aforementioned has application in diaper like structures, it is to be expressly understood that the present invention is not limited to use against a wearer for the absorption of urine and the like, but may be utilized for many other related bandage and bandage-like applications, including, by way of example only and without limitation, surgical dressings, incontinence pads, catamenial pads, and the like.

Referring now to the drawings, FIG. 1 illustrates the present invention as it would be used in an underpad 24. As used herein, the term "underpad" refers to articles which absorb and contain body exudates and more particularly refers to articles which are placed beneath the lower torso of persons confined to beds or wheelchairs or beneath surgical patients to prevent urine, feces, blood, or other exudates from coming in contact with other garments or linens. The underpad 24 comprises an improved absorbent pad 12 constructed in accordance with the principles of the present invention. The absorbent pad 12 has pad side edges 33, pad end edges 34, a pad upper surface 50, and a pad bottom surface 51. In the preferred embodiment shown in FIG. 1, the underpad 24 comprises a liquid pervious topsheet 16; a liquid impervious backsheet 18; and an absorbent pad 12 positioned between said topsheet 16 and said backsheet 18. In the preferred embodiment, the pad 12 is contained between a pair of tissue layers 22 and 26 superposed and subjacent thereto, respectively. The combination of the absorbent pad 12 and the tissue layers 22 and 26 form the absorbent core 20.

The underpad 24 has a liquid receiving top surface 13 which is generally defined by the topsheet 16 and a back surface 15 which is generally defined by the backsheet 18. Preferably, the topsheet 16 and the backsheet 18 have length and width dimensions generally larger than the absorbent core 20, so that they extend beyond the core side edges 19 and the core end edges 21 of the absorbent core 20 where they are affixed together in a suitable manner. As used herein, the term "affixed" encompasses configurations whereby the topsheet 16 is directly joined to the backsheet 18 by affixing the topsheet 16 directly to the backsheet 18 and configurations whereby the topsheet 16 is indirectly joined to the backsheet 18 by affixing the topsheet 16 to intermediate members which in turn are affixed to the backsheet 18. In the preferred embodiment shown in FIG. 1, the extension of the topsheet 16 and/or the backsheet 18 beyond the core side edges 19 and the core end edges 21 of the absorbent core 20 forms the longitudinal edges 23 and the end edges 25, respectively, of the underpad 24. The longitudinal edges 23 and the end edges 25 of the underpad 24 comprise the periphery 27 of the underpad 24.

Examining some of the elements of the underpad 24 in more detail, the topsheet 16 is positioned adjacent to the body surface 48 of the absorbent core 20 and overlays a major portion of the absorbent core 20 so that when exudates are discharged onto the topsheet 16 they penetrate through the topsheet 16 where they are absorbed by the absorbent core 20. The topsheet 16 is compliant, soft-feeling, and non-irritating to the wearer's skin. Further, the topsheet 16 is liquid pervious, permitting liquids to readily penetrate through its thickness. A suitable topsheet 16 may be manufactured from a wide range of materials, such as porous foams, reticulated foams, apertured plastic films, natural fibers (e.g., wood or cotton fibers), synthetic fibers (e.g., polyester or polypropylene fibers) or from a combination of natural and synthetic fibers. Preferably, it is made of hydrophobic material to isolate the wearer's skin from liquids in the absorbent core 20. A particularly preferred topsheet 16 comprises staple length polypropylene fibers having a denier of about 1.5, such as Hercules Type 151 Polypropylene, marketed by Hercules, Inc. of Wilmington, Del. As used herein, the term "staple length fibers" refers to those fibers having a length of at least 15.9 millimeters (0.625 inches). Another particularly preferred topsheet, and one which works particularly well with an absorbent pad 12 of the present invention, is a topsheet having tapered capillaries. Such a topsheet is disclosed and claimed in U.S. Pat. No. 3,929,135, entitled "Absorptive Structure Having Tapered Capillaries," which patent issued to Thompson on Dec. 30, 1975, and which patent is incorporated hereat as fully and completely as if physically reproduced herein.

There are a number of manufacturing techniques which may be used to manufacture the topsheet 16. For example, the topsheet 16 may be woven, non-woven, spunbonded, carded, or the like. A preferred topsheet 16 is carded and thermally bonded by means well known to those skilled in the fabric's art. Preferably, the topsheet 16 has a weight of from about 18 to about 25 grams per square meter, a minimum dry tensile strength of at least about 400 grams per centimeter in the machine direction and a wet tensile strength of at least about 55 grams per centimeter in the cross-machine direction.

The absorbent core 20 may be any means which is generally compressible, conformable, non-irritating to the wearer's skin and capable of absorbing and containing liquids and certain body exudates. A preferred absorbent core 20 has a body surface 48 and a garment surface 49 and comprises an absorbent layer 12 and first and second tissue layers 22 and 26, respectively. The first and second tissue layers 22 and 26 overlay the major surfaces of the absorbent pad 12 to form the body surface 48 and the garment surface 49 of the absorbent core 20.

The absorbent pad 12 may be manufactured in a wide variety of sizes and shapes (e.g., rectangular, hourglass, etc.) and from a wide variety of liquid absorbent materials commonly used in underpads, disposable diapers and other absorbent articles, such as comminuted wood pulp which is generally referred to as airfelt. Examples of other suitable absorbent materials include synthetic staple fibers, such as polypropylene, polyester, nylon, bicomponent fibers, and the like, and also meltblown fibrous webs, cellulosic fibers such as rayon, creped cellulose wadding, absorbent foams, absorbent sponges, super absorbent polymers, absorbent gelling materials, or any equivalent materials or combination of materials. The total absorbent capacity of the absorbent pad 12 should, however, be compatible with the design exudate loading in the intended use of the underpad, diaper, incontinent brief or other article. Further, the size and absorbent capacity of the absorbent pad 12 may be varied to accommodate users ranging from infants to adults.

A preferred embodiment of the underpad 24 has a rectangular shaped absorbent pad 12 and is intended to be placed beneath the user's lower torso. The absorbent pad 12 is preferably a bat of airfelt about 56 centimeters (22.5 inches) wide (lateral dimension), and about 81 centimeters (33.0 inches) long (longitudinal dimension). The airfelt used in the absorbent pad 12 has an uncompressed generally uniform caliper of from about 1.1 millimeter to about 2.3 millimeter (0.04 inch to about 0.09 inch), an absorbent capacity of from about 8 grams to about 20 grams of water per gram of absorbent material, and a weight of from about 0.03 grams per cubic centimeter to about 0.07 grams per cubic centimeter. It should be understood that the size, shape, configuration, weight and total absorbent capacity of the absorbent pad 12 may be varied depending upon the application intended (e.g., the absorbent pad 12 may have a varying caliper, or a hydrophyllic gradient, or may contain absorbent gelling materials).

The first and second tissue layers 22 and 26 improve the tensile strength of the absorbent core 20 and reduce the tendency of the absorbent pad 12 to split, lump or ball when wetted. The first and second tissue layers 22 and 26 also help to improve wicking of the absorbed exudates in directions parallel to the garment surface 49 of the core 20, thereby providing a more even distribution of the exudates throughout the absorbent pad 12. While a number of materials and manufacturing techniques may be used to manufacture the first and second tissue layers 22 and 26, satisfactory results have been obtained with sheets of tissue paper having a basis weight of about 16 grams per square meter (11 lbs. per 3,000 square feet) and having an air permeability of about 30.5 cubic meters per minute per square meter (100 cubic feet per minute per square foot) at a pressure differential of about 12.8 millimeters of water (0.5 inch). While the first and second tissue layers 22 and 26 are preferably coterminus with the absorbent pad 12, they may have different dimensions, a different configuration, or they may be omitted entirely.

The backsheet 18 is positioned adjacent the garment surface 49 of the absorbent core 20 and is preferably attached thereto by attachment means (not shown) such as those well known in the art. For example, the backsheet 18 may be secured to the absorbent core 20 by a uniform continuous layer of adhesive, a patterned layer of adhesive, or an array of separate lines or spots of adhesive.

Adhesives which have been found to be satisfactory are manufactured by National Starch Company of New York, N.Y. and marketed as 34-28-57 and by Eastman Chemical Products Company of Kingsport, Tenn. and marketed under the tradename Eastobond A-3 and by Century Adhesives, Inc., of Columbus, Ohio, and marketed under the tradename Century 5227.

The backsheet 18 is impervious to liquids and is preferably manufactured from a thin plastic film although other flexible liquid impervious materials may also be used. The backsheet 18 prevents the exudates absorbed and contained in the absorbent core 20 from wetting articles which contact the underpad 24, such as bed sheets. Preferably, the backsheet 18 is a polyethylene film having a thickness of from about 0.012 millimeter (0.5 mil) to about 0.051 millimeter (2.0 mils) although other flexible, liquid impervious materials may be used. As used herein, the term "flexible" refers to materials which are compliant and which will readily conform to the general shape and contours of the human body.

A suitable polyethylene film is manufactured by Monsanto Chemical Corporation and marketed in the trade as film No. 8020 and by the Ethyl Visqueen Corporation and marketed as film No. X-813. Backsheet 18 is preferably embossed and/or matte finished to provide a more clothlike appearance. Further, the backsheet 18 may permit vapors to escape from the absorbent core 20 while still preventing exudates from passing through the backsheet 18.

The size of the backsheet 18 and/or the topsheet 16 are dictated by the size of the absorbent pad 12 and the exact underpad, diaper, incontinent brief, or catamenial pad design selected. In a preferred embodiment, the backsheet 18 and the topsheet 16 have a rectangular shape and extend beyond the absorbent pad 12 a minimum distance of at least about 1.0 centimeter to about 5.0 centimeters (0.4 to about 2.0 inches) where they are joined directly to each other in the longitudinal edges 23 of the underpad 24 by attachment means (not shown) as are well known in the art. The attachment means may be, for example, a uniform continuous layer of adhesive, a patterned layer of adhesive or an array of separate lines or spots of adhesive.

In addition to sheer absorptive capacity, two desirable attributes of a disposable absorbent underpad, diaper, incontinent brief, or catamenial pad and of the absorptive pad for use therein, are surface dryness and softness impression. Airfelt density is one of the major factors controlling these attributes. The favorable density ranges are, however, different for the two attributes. Typically, low density favors a good softness impression while presenting a poor skin dryness impression. Alternatively, high density favors a good skin dryness impression while providing a poor softness impression.

In other words, typically, low density favors a good softness/flexibility impression while high density favors a good liquid distribution/skin dryness impression. The good liquid distribution/skin dryness impression of the high density regions results from the fact that the high density regions have better capillary action than the low density regions. As used herein, the term "capillaries" refers to the spaces through which liquids may flow. In a fibrous pad, the capillaries are those spaces between individual fibers or groups of fibers. In non-fibrous materials, such as foams, the capillaries might be a series or pattern of "tunnels" extending throughout the foam. Further, the term "wicking" or "capillary action" refers to the movement of liquid through the capillaries. The liquid is moved through the capillaries by gravity, the hydrostatic head of the liquid, and the "sucking" or "draw" of the capillaries. The sucking or draw force causing a liquid to enter a cylindrical capillary is expressed by the equation:

$$P = (2 \text{ nu } \cos \text{ theta})/r$$

wherein
the force is represented by the capillary pressure, and
P is the capillary pressure,
nu is the surface tension of the liquid,
theta is the liquid-fiber contact angle, and
r is the capillary radius.

With a given liquid, the pressure (capillary force) increases with the cosine of the liquid-fiber contact angle (reaching a maximum where the angle is zero) and also increases with narrower capillary radii so that narrower capillaries will draw liquid from wider ones. What appears to be only a small difference in capillary pressure is all that is required for one capillary to attract and drain liquid from an adjacent capillary.

In an absorbent core made of fibrous material, such as airfelt, and having a uniform relatively low density throughout, the capillaries are relatively large. These large capillaries provide good liquid storage or absorption but do not wick the liquids away from the point of liquid acquisition very quickly. Therefore, the area around the point of liquid acquisition quickly becomes saturated and the liquid "puddles". In an underpad, diaper, brief, or catamenial pad, these puddles will either be adjacent to the wearer's skin, thereby causing poor skin dryness impression and possibly skin irritation, or the liquid may leak onto other garments and linens.

However, if the fibrous absorbent core is uniformly compressed to a relatively high density, the wicking characteristics change dramatically. As the core is compressed, the individual fibers are forced closer towards one another, thereby decreasing the size of the capillaries between those fibers. The smaller capillaries have less storage or absorption capabilities than the larger capillaries, but they wick liquids away from the point of acquisition much faster than the larger capillaries.

Therefore, it would seem desirable to develop an absorbent pad that would combine the qualities of good liquid absorption and fast wicking of relatively large amounts of liquid away from the point of liquid acquisition to unsaturated regions of the pad. This concept is not new. However, none of the prior art inventions have developed an absorbent pad that so efficiently utilizes the total absorbent capacity of the pad by wicking liquid quickly, in large quantities, and in predetermined directions, as well as the present invention does.

Figure 2:
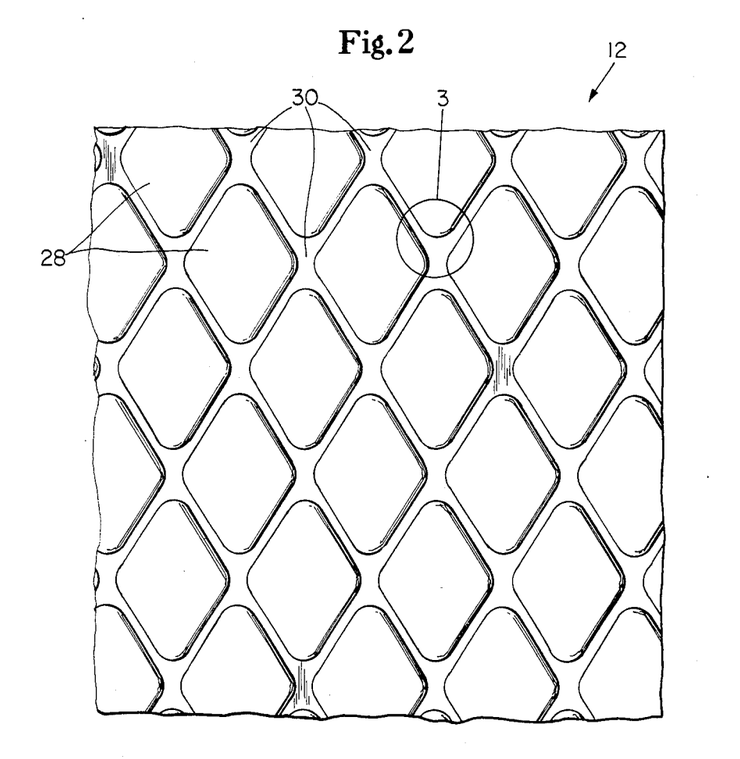
FIG. 2 is a preferred embodiment of a densification pattern of the present invention comprising tuft regions and channels.

FIG. 2 shows a preferred wicking pattern comprising an array of tuft regions 28 and channels 30. The term "tuft regions" refers to substantially undensified, i.e., relatively low density regions. The term "channels" refers to those regions which separate and surround the tuft regions 28, and which, at least in certain regions, have a greater density than the tuft regions 28. As used herein, the terms "low density, intermediate density, and high density" are relative terms that are used in comparison to each other and unless specifically quantified herein, are not intended to refer to any specific density or any degree of density.

In the preferred embodiment shown in FIG. 2, the channels 30 comprise storage regions 37 and transport regions 39. As used herein, the term "storage regions" refers to regions of the pad 12 having a density greater than the density of the tuft regions 28 but less than the density of the transport regions 39. Further, as used herein, the term "transport regions" refers to regions of the pad 12 having a density greater than the density of the storage regions 37, which as hereinbefore mentioned have a density greater than the density of the tuft regions 28. Resultingly, the pad 12 comprises three different densities, the relatively low density tuft regions 28, the greater density storage regions 37 and the still greater density transport regions 39.

Figure 3:
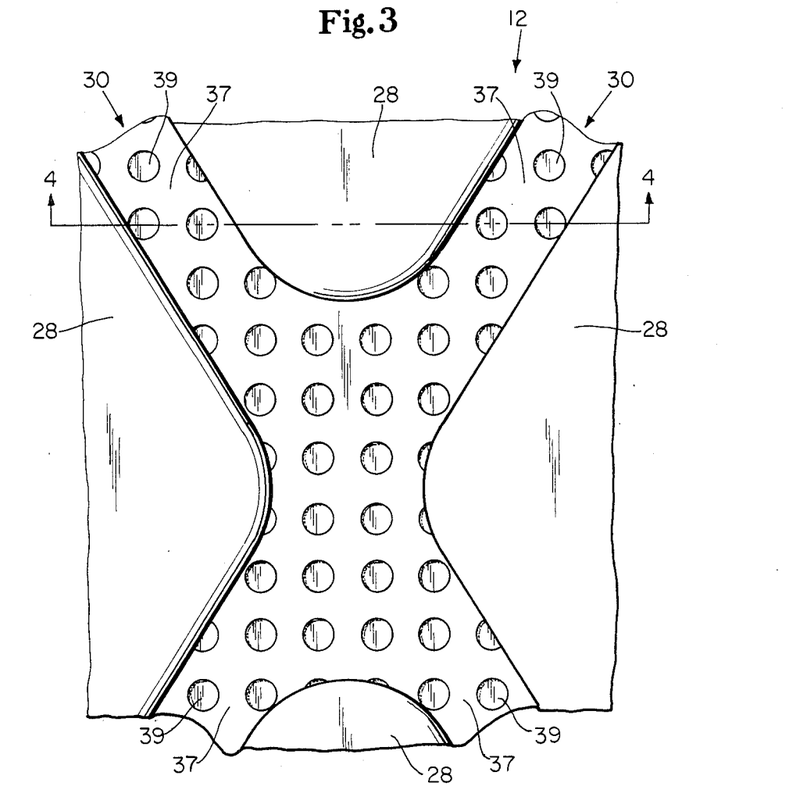
FIG. 3 is an enlarged view of the circular section labeled "3" in FIG. 2 and which better illustrates that the channels comprise storage regions and transport regions.
Figure 4:
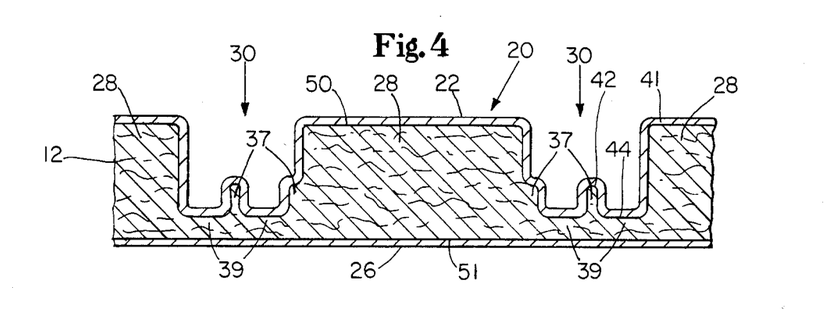
FIG. 4 is a cross-sectional view taken along section line 4—4 of FIG. 3.

FIG. 3 is an enlarged top plan view of the circular area labeled "3" in FIG. 2, illustrating the storage regions 37 and the transport regions 39 of the channels 30 of the preferred embodiment. In this preferred embodiment the transport regions 39 are generally circular and are separated and surrounded by the storage regions 37 which extend continuously and sinuously throughout the channels 30. However, the transport regions 39 need not be circular and can be of any shape and size and the storage regions 37 need not be continuous or sinuous. As used herein, the term "surrounds" refers to completely encircling a transport region 39 with storage regions 37 so that the transport region 39 is bounded on all sides by the storage regions 37 or by completely encircling a transport region 39 with a combination of storage regions 37 and a single tuft region 28 so that the transport region 39 is bounded on at least one side by a storage region 37. In another preferred embodiment, as shown in FIGS. 3 and 4, at least one transport region 39 is entirely surrounded solely by the storage regions 37. As used herein, the term "entirely surrounded solely" refers to completely encircling a transport region 39 with storage regions 37 so that the transport region 39 is not in contact with a tuft region 28. As used herein, the terms "continuous" and "sinuous" refer to unbroken and uninterrupted linear and non-linear regions which extend between at least two adjacent tuft regions 28 in a direction parallel or generally parallel to a side edge of one of said tuft regions 28. In this preferred embodiment, the transport regions 39 are preferably from about 0.001 milimeters to about 5.0 milimeters apart from each other, more preferably from about 0.5 milimeters to about 3.0 milimeters, and most preferably 1.5 milimeters.

FIG. 4 is a cross-sectional view of the absorbent pad 12 ataken along line 4—4 in FIG. 3, including the addition of tissue layers 22 and 26. As seen, in this preferred embodiment the tuft regions 28 have a caliper greater than the storage regions 37 which, in turn, have a caliper greater than the transport regions 39. Further, the absorbent pad 12, and resultingly the tuft regions 28, the storage regions 37, and the transport regions 39 have co-planar back surfaces 40. The top surfaces of the tuft regions 28, the storage regions 37, and the transport regions 39 are non-coplanar and are designated 41, 42 and 44, respectively. Preferably, the low density tuft regions 28 have a caliper, measured from the back surface 40 to the tuft top surface 41, or from about 0.25 milimeters to about 25.00 milimeters, more preferably of from about 0.75 milimeters to about 12.50 milimeters, and most preferably 1.12 milimeters. Preferably, the intermediate density storage regions 37 have a caliper, measured from the back surface 40 to the storage region top surface 42, of from about 0.10 milimeters to about 10.20 milimeters, more preferably of from about 0.25 milimeters to about 5.10 milimeters, and most preferably 0.43 milimeters. Preferably, the high density regions 39 have a caliper, measured from the back surface 40 to the transport region top surface 44, of from about 0.0001 milimeters to about 2.72 milimeters, more preferably of from about 0.08 milimeters to about 1.44 milimeters, and most preferably 0.12 milimeters. Further, the present invention can be practiced with transport regions 39 having a caliper of 0.00, i.e., the transport regions 39 are non-existant. Even if the transport regions 39 are non-existant, for purposes of this invention, the transport regions 39 are considered as having a density greater than the density of the storage regions 37.

As hereinbefore mentioned, the density of an absorbent material is a critical parameter when one is concerned with liquid distribution, capillary action, or wicking throughout an absorbent pad. The density of an absorbent material can be determined by dividing the material's basis weight by its thickness. The basis weight is obtained by weighing a uniform section of the material and dividing that weight by the section's superficial area. Thickness can be determined for the section in question by means of a caliper or any similar precision instrument. The superficial area of very small sections can be determined with the use of a microscope or an electron microscope. Preferably, the low density tuft regions 28 have a density of from about 0.004 grams per cubic centimeter to about 0.370 grams per cubic centimeter, more preferably of from about 0.007 grams per cubic centimeter to about 0.120 grams per cubic centimeter, and most preferably 0.080 grams per cubic centimeter. Preferably, the intermediate density storage regions 37 have a density of from about 0.009 grams per cubic centimeter to about 0.920 grams per cubic centimeter, more preferably of from about 0.020 grams per cubic centimeter to about 0.370 grams per cubic centimeter, and most preferably 0.220 grams per cubic centimeter. Preferably, the high density transport regions 39 have a density of from about 0.001 grams per cubic centimeter to about 1000.000 grams per cubic centimeter, more preferably of from about 0.640 grams per cubic centimeter to about 1.140 grams per cubic centimeter, and most preferably 0.780 grams per cubic centimeter.

It is to be expressly understood that while the present invention has been illustrated such that the tuft regions 28, the storage regions 37, and the transport regions 39 have different calipers and non-co-planar top surfaces, the essence of this invention lies not in the provision of a pad having varying calipers, but lies instead in the combination of tuft regions 28 which are separated and surrounded by channels 30, wherein the channels comprise storage regions 37 and transport regions 39. In fact, the absorbent pad 12 could have a uniform caliper and planar surfaces throughout, or the storage regions 37 could have a greater caliper than the tuft regions 28, or the transport regions 39 could have a greater caliper than the storage regions 37, or any combination or configuration of calipers and densities could be present. Further, while the channels 30 have been illustrated as comprising storage regions 37 which separate and surround transport regions 39, the channels 30 alternatively could comprise transport regions 39 which separate and surround storage regions 37.

The channels 30, such as those formed in accordance with the present invention, serve two functions. First, channels 30 comprising regions having different calipers help to mechanically bond the tissue layers 22 and 26 with the pad 12 through fiber entanglement and friction, thereby holding the tissue layers 22 and 26 in close contact with the pad 12 and providing the pad 12 with improved integrity. Secondly, channels 30 having regions of different density provide the pad 12 with improved wicking, in contrast to a pad having channels of only a single density. The transport regions 39, due to their high density, have very small capillaries between their fibers, as hereinbefore explained. Therefore, as hereinbefore explained, the transport regions 39 provide very fast wicking. The storage regions 37 have a density less than the density of the transport regions 39 and, therefore, have larger capillaries between their fibers than the transport regions 39. This gives the storage regions 37 the tendency to absorb more liquid than the transport regions 39. In a sense, the storage regions 37 store liquid for use by the transport regions 39. In use, liquid which is deposited onto the pad 12 is absorbed to some degree by the tuft regions 28. However, the tuft regions 28 adjacent to the area where the liquid was deposited, may not be able to absorb all of the liquid fast enough to prevent "puddling" of the liquid on the absorbent pad 12, which resultantly may give the wearer an uncomfortably wet feeling or cause skin irritation. However, the excess liquid will enter the channels 30 which are intended to direct the liquid to other regions of the pad 12 and to other tuft regions 28 which are unsaturated enough so that they will accept and absorb the excess liquid. However, if the channels 30 are not able to wick enough liquid away from the point of acquisition quickly enough, there may still be "puddling." If the channels 30 were comprised solely of high density transport regions 39, they would wick liquid very fast, but, due to their small capillaries, they would not be able to transport much volume of liquid. However, the addition to the channels 30 of the storage regions 37 provides the transport regions 39 with a supply of liquid. In use, liquids are wicked relatively quickly through the transport regions 39, stored and relatively slowly wicked in the storage regions 37, drawn into and quickly wicked through the next succeeding transport regions 39, thereby emptying the preceding storage regions 37 which are then ready and able for refilling. It is the combination of high density transport regions 39 and intermediate density storage regions 37 and how they are configured relative to each other in the channels 30 which provides the channels 30 with the capability of being able to wick relatively large volumes of liquid quickly. This improvement is provided by the cyclical wick, store, wick, store, ... action of the transport regions 39 and the storage regions 37.

Referring back now to FIG. 2, FIG. 2 shows a preferred arrangement of tuft regions 28 and channels 30. The preferred arrangement shown in FIG. 2 comprises an array of rhombus shaped tuft regions 28 separated and surrounded by channels 30. The tuft regions 28 are staggered in the lateral direction so that each corner of each tuft 28 is nestled between two adjacent tuft regions 28. The tuft regions 28 are diamond shaped and have a longitudinal dimension "Y" of about 41 millimeters and a lateral dimension "X" of about 26 millimeters. The channels 30 are about 2 millimeters wide. The channels 30 are bilaterally extending, generally linear, and sinuous.

Figure 5:
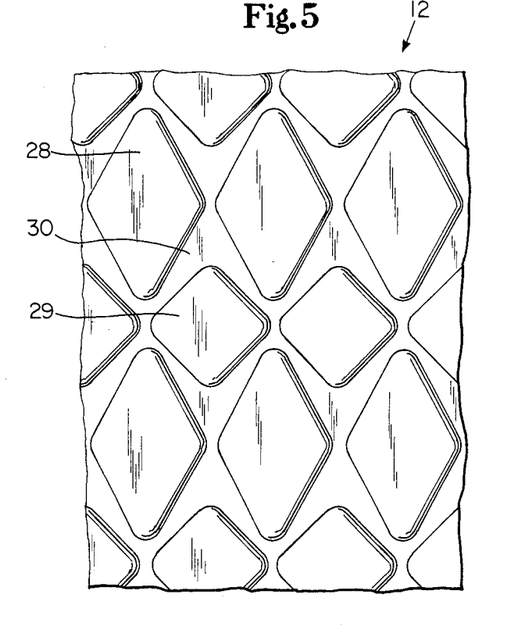
FIG. 5 is an alternatively preferred densification pattern of the present invention showing only the tuft regions and the channels.

A more preferred arrangement is shown in FIG. 5. In the more preferred embodiment shown in FIG. 5, the tuft regions 28 and the channels 30 are arranged such that the absorbent pad 12 comprises alternating horizontal rows in the longitudinal direction of rhombus shaped tuft regions 28 and square shaped tuft regions 29, the square shaped tuft regions 29 having been rotated so that two corners are parallel to the longitudinal axis 80 and two corners are parallel to the lateral axis 90. In other words, moving longitudinally up or down the pad 12 one encounters a horizontal row of rhombus shaped tuft regions 28, and then a horizontal row of square shaped tuft regions 29, and then a horizontal row of rhombus shaped tuft regions 28, and so on. In the lateral direction, the vertical rows of rhombus shaped tuft regions 28 and square shaped tuft regions 29 are staggered. In other words, moving in the lateral direction across the pad 12 one encounters a vertical row of rhombus shaped tuft regions 28, and then a vertical row of square shaped tuft regions 29, and then a vertical row of rhombus shaped tuft regions 28, and so on. The rhombus shaped tuft regions 28, in the preferred embodiment shown in FIG. 5, have a longitudinal dimension of about 41 millimeters and a lateral dimension of about 26 millimeters. Rhombus shaped tuft regions 28, such as these, which are longer in the longitudinal direction than they are wide in the lateral direction, cause liquids to wick faster in the longitudinal direction through the channels 30, than in the lateral direction through the channels 30. Therefore, more of the absorbent pad 12 in the longitudinal direction is utilized. However, if solely rhombus shaped tuft regions 28 are used, the laterally extending regions of the absorbent pad 12 may not be totally and efficiently used. Therefore, square shaped tuft regions 29, which have no preference for wicking liquids through the channels 30 in either the longitudinal or lateral directions, are provided. The square shaped tuft regions 29 have a diagonal dimension from corner to corner of about 26 millimeters. The combination of the rhombus shaped tuft regions 28 and the square shaped tuft regions 29 causes more liquid to be wicked longitudinally through the channels 30 than laterally, yet still ensures that enough liquid is wicked in the lateral direction through the channels 30 so that all of the regions in the absorbent pad 12 are efficiently utilized. Circular tuft regions would also serve the same function as the square shaped tuft regions 29 since they too have no preference for wicking in one direction or another. It is within the scope of the present invention that the dimensions and orientations of the rhombus and square shaped tuft regions 28 and 29 may be varied, depending on the shape and size of the absorbent pad 12. For instance, if more wicking is desired in the lateral direction, the longitudinal dimension of the rhombus shaped tuft regions 28 may be decreased and the lateral dimension of the rhombus shaped tuft regions 28 increased.

Figure 6:
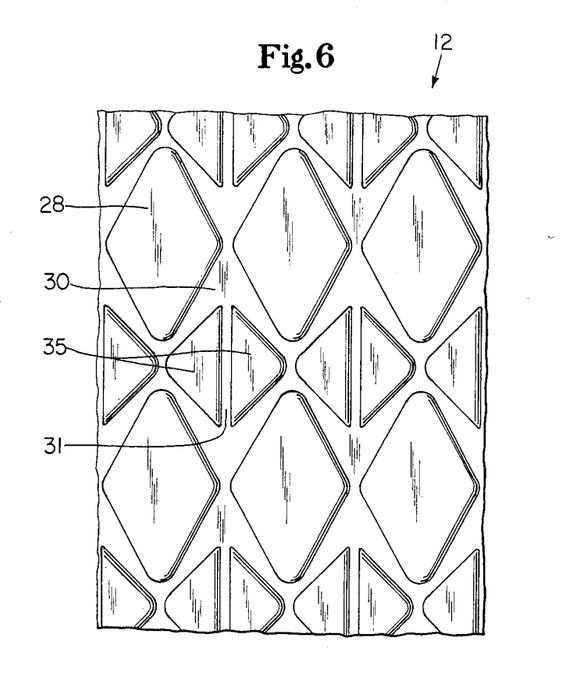
FIG. 6 is still another alternatively preferred densification pattern of the present invention showing only the tuft regions and the channels.

In accordance with the present invention, and with reference now more particularly to FIG. 6, a most preferred arrangement of tuft regions is shown in which the pattern densification of the absorbent pad 12 has been modified to provide improved wicking in the longitudinal direction by the addition to the pattern of the longitudinally extending channels 31. The longitudinally extending channels 31 are situated so that they intersect and divide the square shaped tuft regions 29, thereby forming pairs of triangle tuft regions 35. Therefore, the pad 12 now comprises alternating horizontal rows in the longitudinal direction of rhombus shaped tuft regions 28 and pairs of triangle tuft regions 35, the rhombus shaped tuft regions 28 and the pairs of triangle tuft regions 35 being staggered in the lateral direction. Alternatively, improved wicking in the lateral direction could be had by providing laterally extending and tuft regions 28 or 29 intersecting channels in the lateral direction. Also, alternatively, the intersecting channels 31 could intersect either or both the rhombus shaped tuft regions 28 and the square shaped tuft regions 29.

The longitudinally extending channels 31 preferably have a density equal to the density of the channels 30 and are formed in the absorbent pad 12 by the same method and manner as the channels 30.

In accordance with the present invention, and again with reference to FIG. 1, wicking barrier lines 43 are provided in the absorbent pad 12. The wicking barrier lines 43 are regions of relatively high density and are intended to wick liquids along their length to less saturated regions of the absorbent pad 12 so that the liquids can be absorbed before leaking beyond the edges of the absorbent pad 12. The wicking barrier lines 43 surround or substantially surround the densification pattern and are intended to prevent liquids contained within the absorbent core 20 from reaching the core side edges 19 and the core end edges 21 of the absorbent core 20 and leaking beyond. The wicking barrier lines 43 are preferably continuous around the entire densification pattern, but can be discontinuous, and are preferably straight lines, but can be curved lines, or a series of circles, or squares, or triangles, or any other shape or configuration. The wicking barrier lines 43 preferably border the edges of the densification pattern but can be located beyond or within its edges. In the preferred embodiment, the wicking barrier lines 43, like the channels 30, comprise storage regions 37 which separate and surround transport regions 39. Further, preferably the wicking barrier lines 43 are from about 1.0 millimeter to about 15.0 centimeters from the pad side edges 33 or the pad end edges 34.

Figure 7:
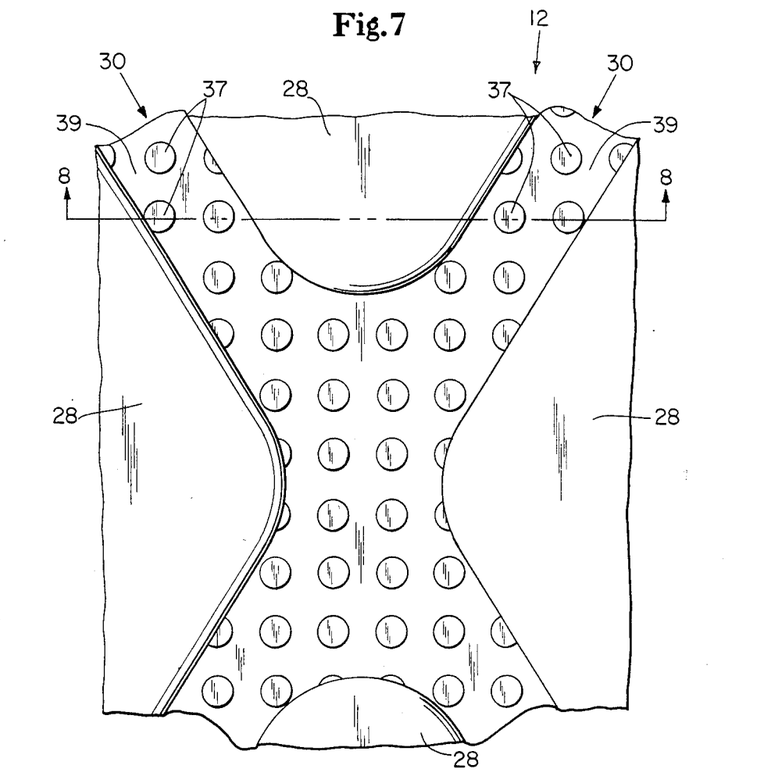
FIG. 7 is an enlarged view of the circular area labeled "3" in FIG. 2 showing yet another alternatively preferred densification pattern and which better illustrates an alternative arrangement of the storage regions and the transport regions.
Figure 8:
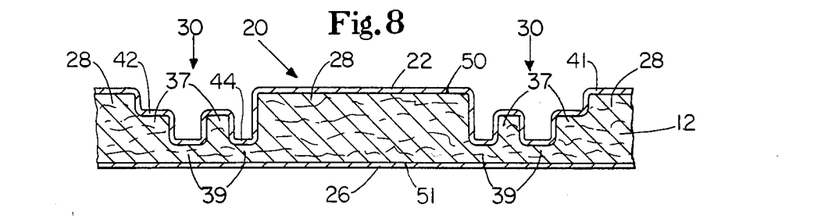
FIG. 8 is a cross-sectional view taken along line 8—8 of FIG. 7.

An alternatively preferred embodiment of the present invention is shown in FIG. 7. FIG. 7 is an enlarged view of the circular area labeled "3" in FIG. 2 and shows an alternatively preferred densification pattern within the channels 30. A cross-sectional view of this embodiment taken along line 8—8 in FIG. 7 is shown in FIG. 8, including the addition of tissue layers 22 and 26. In this embodiment, the storage regions 37 now appear as generally circular nubbles which project upwardly from the transport regions 39. The transport regions 39 separate and surround the storage regions 37 and are continuous and sinuously extending. Therefore, in this preferred embodiment, the tuft regions 28 have a caliper greater than the storage regions 37 which, in turn have a caliper greater than the transport regions 39. As used herein, the term "surrounds" refers to completely encircling a storage region 37 with transport regions 39 so that the storage region 37 is bounded on all sides by the transport regions 39 or by completely encircling a storage region 37 with a combination of transport regions 39 and a single tuft region 28 so that the storage region is bounded on at least one side by a transport region 39. In another preferred embodiment, as shown in FIGS. 7 and 8, at least one storage region 37 is entirely surrounded solely by the transport regions 39. As used herein, the term "entirely surrounded solely" refers to completely encircling a storage region 37 with transport regions 39 so that the storage region 37 is not in contact with a tuft region 28.

A method and apparatus for densifying the absorbent pad 12 and for forming the densification patterns in accordance with the present invention are disclosed in U.S. Pat. No. 3,908,659, entitled "Absorbent Pad Structure, Diaper Construction Utilizing Same And Methods Of Manufacture Thereof", which patent issued to Wehrmeyer et al. on Sept. 30, 1975, and which patent is incorporated herein by reference as fully and completely as if reproduced herein.

Basically, without intending to limit the present invention, the present invention is an absorbent pad, preferably made of airfelt, which has been embossed by dry pattern densification to provide improved wicking of liquids away from the point of liquid acquisition to thereby improve the absorption capability of the pad, and to further provide improved pad integrity, flexibility, and skin dryness impression. The densification pattern comprises relatively low density tuft regions which are separated and surrounded by channels which further comprise intermediate density storage regions and high density transport regions. As urine or other liquids are deposited onto the pad, they are absorbed as much as possible by the tuft regions adjacent to the point of liquid acquisition. Excess liquid which cannot be quickly absorbed by the tuft regions is wicked through the channels to other regions of the diaper which are able to accept and absorb the excess liquid. The liquids wick quickly through the channels 30 by the cyclical wick, store, wick, store,... action of the high density transport regions and the intermediate density storage regions. Resultingly, liquids are transported to unsaturated tuft regions which are able to absorb the excess liquid, thereby decreasing and preferably eliminating the amount of excess liquid which is available to "puddle" on the absorbent pad, or leak beyond its edges.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed is:

1. An absorbent pad, comprising:
   tuft regions; and
   channels, said channels separating and surrounding said tuft regions; said channels further comprising storage regions and transport regions, said storage regions having a density greater than the density of said tuft regions, said transport regions having a density greater than the density of said storage regions, and said transport regions being separated and surrounded by said storage regions.

2. The absorbent pad as claimed in claim 1, wherein at least one of said transport regions is entirely surrounded solely by said storage regions.

3. An absorbent pad, comprising:
   tuft regions; and
   channels, said channels separating and surrounding said tuft regions, said channels further comprising storage regions and transport regions, said storage regions having a density greater than the density of said tuft regions, said transport regions having a density greater than the density of said storage regions, and said storage regions being separated and surrounded by said transport regions.

4. The absorbent pad as claimed in claim 3, wherein at least one of said storage regions is entirely surrounded solely by said transport regions.

5. The absorbent pad as claimed in claim 1 or 3, further comprising a pad upper surface, a pad bottom surface and a tissue layer, wherein said tissue layer is adjacent to one of said surfaces.

6. The absorbent pad as claimed in claim 5, further comprising a pad side edge and a wicking barrier line wherein said wicking barrier line is located near to and substantially parallel to said pad side edge.

7. The absorbent pad as claimed in claims 1 or 3, wherein said tuft regions have a density of from about 0.004 grams per cubic centimeter to about 0.370 grams per cubic centimeter.

8. The absorbent pad as claimed in claim 7, wherein said storage regions have a density of from about 0.009 grams per cubic centimeter to about 0.920 grams per cubic centimeter.

9. The absorbent pad as claimed in claim 8, wherein said transport regions have a density of from about 0.001 grams per cubic centimeter to about 1000.000 grams per cubic centimeter.

* * * * *

UNITED STATES PATENT AND TRADEMARK OFFICE
CERTIFICATE OF CORRECTION

PATENT NO. : 4,781,710

DATED : 11/1/88

INVENTOR(S) : Donald R. Megison, Richard A. Vonderhaar

It is certified that error appears in the above-identified patent and that said Letters Patent is hereby corrected as shown below:

Column 4, line 8:     "bedpan" should read ---bedpad---.

Column 9, line 42:    "ataken" should read ---taken---.

Column 14, line 6:    "capability" should read ---capabilities---.

Column 14, line 68, Claim 6:  after "wicking barrier line", insert ---,---.

Column 1, line 10:    "Absorbents" should read ---Absorbent---.

Column 4, line 53:    after "surface" delete ---15---.

Signed and Sealed this

Twenty-third Day of May, 1989

Attest:

DONALD J. QUIGG

*Attesting Officer*    Commissioner of Patents and Trademarks